(12) United States Patent
Patterson et al.

(10) Patent No.: US 7,137,987 B2
(45) Date of Patent: Nov. 21, 2006

(54) DISTAL RADIUS BONE PLATING SYSTEM WITH LOCKING AND NON-LOCKING SCREWS

(75) Inventors: Chad J. Patterson, Bartlett, TN (US); F. Barry Bays, Collierville, TN (US); Jeffrey G. Roberts, Germantown, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 385 days.

(21) Appl. No.: 10/884,448

(22) Filed: Jul. 2, 2004

(65) Prior Publication Data

US 2006/0004362 A1    Jan. 5, 2006

(51) Int. Cl.
*A61B 17/58* (2006.01)
(52) U.S. Cl. ....................................................... 606/69
(58) Field of Classification Search ................. 606/69, 606/61, 70–71
See application file for complete search history.

(56) References Cited

U.S. PATENT DOCUMENTS

| 5,522,902 | A | 6/1996 | Yuan et al. |
| 5,601,553 | A | 2/1997 | Trebing et al. |
| 5,709,686 | A | 1/1998 | Talos et al. |
| 6,206,881 | B1 | 3/2001 | Frigg et al. |
| 6,283,969 | B1 | 9/2001 | Grusin et al. |
| 6,623,486 | B1 * | 9/2003 | Weaver et al. ............... 606/69 |
| 6,755,832 | B1 | 6/2004 | Happonen et al. |
| 6,755,833 | B1 | 6/2004 | Paul et al. |
| 6,866,665 | B1 | 3/2005 | Orbay |
| 2002/0156474 | A1 | 10/2002 | Wack et al. |
| 2004/0116930 | A1 | 6/2004 | O'Driscoll et al. |
| 2004/0122429 | A1 | 6/2004 | Phillips et al. |
| 2004/0153073 | A1 * | 8/2004 | Orbay ........................ 606/69 |
| 2004/0167522 | A1 * | 8/2004 | Niederberger et al. ........ 606/69 |
| 2005/0065524 | A1 | 3/2005 | Orbay |
| 2005/0080421 | A1 | 4/2005 | Weaver et al. |
| 2005/0089818 | A1 | 4/2005 | Huebner |

FOREIGN PATENT DOCUMENTS

WO    WO 00/53111    9/2000

* cited by examiner

*Primary Examiner*—Eduardo C. Robert
*Assistant Examiner*—Anitza M. San Miguel
(74) *Attorney, Agent, or Firm*—Duane Morris LLP

(57) ABSTRACT

A bone plating system for fixating distal or proximal ends of long bones includes a bone plate having a head portion and a shaft portion, and a plurality of bone screws, at least one of which is a locking bone screw and at least one non-locking cancellous bone screw. The bone plate has a plurality of plate holes in the head portion and a plurality of plate holes in the shaft portion. The head portion or the shaft portion of the bone plate may have a plurality of threaded plate holes for engaging the at least one locking bone screw and at least one non-threaded plate hole for engaging the non-locking cancellous bone screw. The non-locking cancellous bone screw and the at least one non-threaded plate hole are configured and dimensioned to have a particularly useful dimensional relationship.

20 Claims, 7 Drawing Sheets

DISTAL RADIUS BONE PLATING SYSTEM WITH LOCKING AND NON-LOCKING SCREWS

FIELD OF THE INVENTION

The present invention relates to a bone plating system and method for fracture fixation of bone.

BACKGROUND

For bone fractures such as peri-articular fractures, bone plating systems that provide fixed angular relationship between the bone plate and the bone screw are known to be beneficial. Many of these devices require suitable bone quantity and quality, and a fracture pattern that is compatible with the device to be effective. Where these requirements are not satisfied, e.g. bone fractures involving severely comminuted bone or missing bone segments, conventional bone plate and screw systems must be used. Although these conventional systems are particularly well-suited to promoting healing of the fracture by compressing the fracture ends together and drawing the bone into close apposition with other fragments and the bone plate, the angular relationships between the plate and screws are not fixed and can change postoperatively. This can lead to malalignment and poor clinical results.

The primary mechanism for the change in angular relationship between the bone plate and the bone screws is the movement between the bone plate and the compressed bone caused by the dynamic loading from physiological conditions. The shear forces generated by the dynamic loading often cause the bone plate and screws to come loose and release the stored energy in the compressed bone.

Securing or locking the bone screws to the bone plate provides a fixed angular relationship between the plate and screw and reduces the incidence of loosening. One method of securing the bone screws to the bone plate involves the use of locking screws. A locking screw has threading on an outer surface of its head that mates with corresponding threads on the surface of a plate hole to lock the screw to the plate. Bone plates having threaded holes for accommodating locking screws are known. As the relationship between the locking screws and the bone plate is fixed, locking screws provide a high resistance to shear or torsional forces. However, locking screws have a limited capability to compress bone fragments.

In summary, conventional non-locking bone screws, i.e. screws that do not lock in a fixed angular relationship to a bone plate, effectively compress bone fragments, but generally possess a low resistance to shear forces that can lead to loosening of the screw. Locking screws, on the other hand, have a high resistance to shear forces ensuring stability at the bone screw-to-plate hole interface, but possess a limited ability to compress the bone fragments. Thus, a bone plating system that combines non-locking screws with locking screws in long bone applications has been introduced in the industry. One such example is a bone plating system disclosed in U.S. Pat. No. 6,623,486 to Weaver et al.

Thus, it can be appreciated that there exists a continuing need for a new and improved bone plating system that would enhance the effectiveness and useability of these bone plating systems.

SUMMARY OF THE INVENTION

A bone plating system for fixation of bone according to an embodiment of the present invention comprises a bone plate having an upper surface, a lower surface, at least one non-threaded plate hole and at least one threaded plate hole. The bone plating system also includes at least one locking bone screw having a shaft with a first thread for engaging bone and a head with a second thread configured and dimensioned to mate with the thread of the threaded plate hole. At least one non-locking cancellous bone screw is also included that has a shaft with a cancellous thread for engaging the cancellous tissue of a bone and a head whose diameter is larger than the non-threaded plate hole diameter. The locking and non-locking bone screws remain seated in their respective plate holes for substantially as long as the bone plate is implanted.

The at least one non-locking cancellous bone screw has a core diameter smaller than the non-threaded plate hole diameter. The non-locking cancellous bone screw's thread diameter is larger than the diameter of the non-threaded plate hole and the cancellous thread has a pitch that is sufficiently large to clear the sidewall thickness of the non-threaded plate hole. These particular features of the non-locking cancellous bone screw allow it to be threaded into the non-threaded plate hole and allow the screw head to compress against the edges of the bone plate that define the non-threaded plate hole. If the non-threaded plate hole were to be made large enough to completely clear the cancellous thread of the cancellous bone screw, the plate hole would be too large to catch the screw head. Also, making the head of the screw larger would make the screw head impractical, and be counter to the long established goal of size reduction for in vitro devices used in minimally invasive surgical procedures. The non-locking screw may be screwed into the patient's bone within a range of angles as required by the particular shape of the fracture being fixated. Furthermore, the non-locking bone screw's core diameter is larger than the threaded plate hole diameter preventing the non-locking bone screw from being accidentally threaded into the threaded plate holes.

According to another embodiment of the present invention, a bone plating system for fixation of bone comprises a bone plate having an upper surface, a lower surface, a head portion, a shaft portion, and a plurality of plate holes for receiving bone screws. At least one non-threaded plate hole and at least one threaded plate hole are provided in the head portion of the bone plate.

The bone plating system of the present invention also includes at least one locking bone screw and at least one non-locking cancellous bone screw. The locking bone screw has a shaft with a thread for engaging bone and a head with a thread configured and dimensioned to mate with the thread of the threaded plate hole. The non-locking, cancellous bone screw has a shaft with a thread for engaging the cancellous tissue of a bone and a head whose diameter is larger than the diameter of the non-threaded plate hole. The non-locking cancellous bone screw has a core diameter smaller than the diameter of the non-threaded plate hole. The non-locking cancellous bone screw's thread diameter is larger than the diameter of the non-threaded plate hole and the cancellous thread has a pitch that is sufficiently large to clear the sidewall thickness that defines the non-threaded plate hole. This particular dimensional relationship between the non-locking cancellous bone screw and the non-threaded plate hole requires the cancellous bone screw to be threaded into the non-threaded plate hole. Further, as in the previous embodiment of the present invention, the non-locking bone screw's core diameter is larger than the threaded plate hole diameter preventing the non-locking bone screw from being threaded into the threaded plate holes accidentally.

In using the bone plating system of the present invention, to maximize the benefit of combining non-locking bone screws with locking bone screws, both the locking and non-locking bone screws remain seated in their respective plate holes for substantially as long as the bone plate is implanted.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1a is a top view of an embodiment of a bone plate according to an aspect of the present invention.

FIG. 1b is a cross-sectional view of a threaded plate hole of the bone plate of FIG. 1a through line B—B.

FIG. 1c is a cross-sectional view of a non-threaded hole in the head portion of the bone plate of FIG. 1a through line A—A in FIG. 1a.

FIG. 1d is a cross-sectional view of the non-threaded hole of FIG. 1c through line C—C in FIG. 1a.

FIG. 1e is a top view of another embodiment of the bone plate of FIG. 1a.

FIG. 2 is a side view illustration of the bone plate of FIG. 1a.

FIG. 3 is an end view illustration of the bone plate of FIG. 1a.

FIG. 4 is a perspective view of the bone plate of FIG. 1a.

FIG. 7 is a side view of a non-locking cortical bone screw for use in conjunction with the shaft plate hole of the bone plate of FIG. 1a.

FIG. 8 is a cross-sectional illustration of the non-locking bone screw of FIG. 6 being threaded into the non-threaded plate hole of the bone plate of FIG. 1a.

Figures 1A, 1B, 1C, 1D:
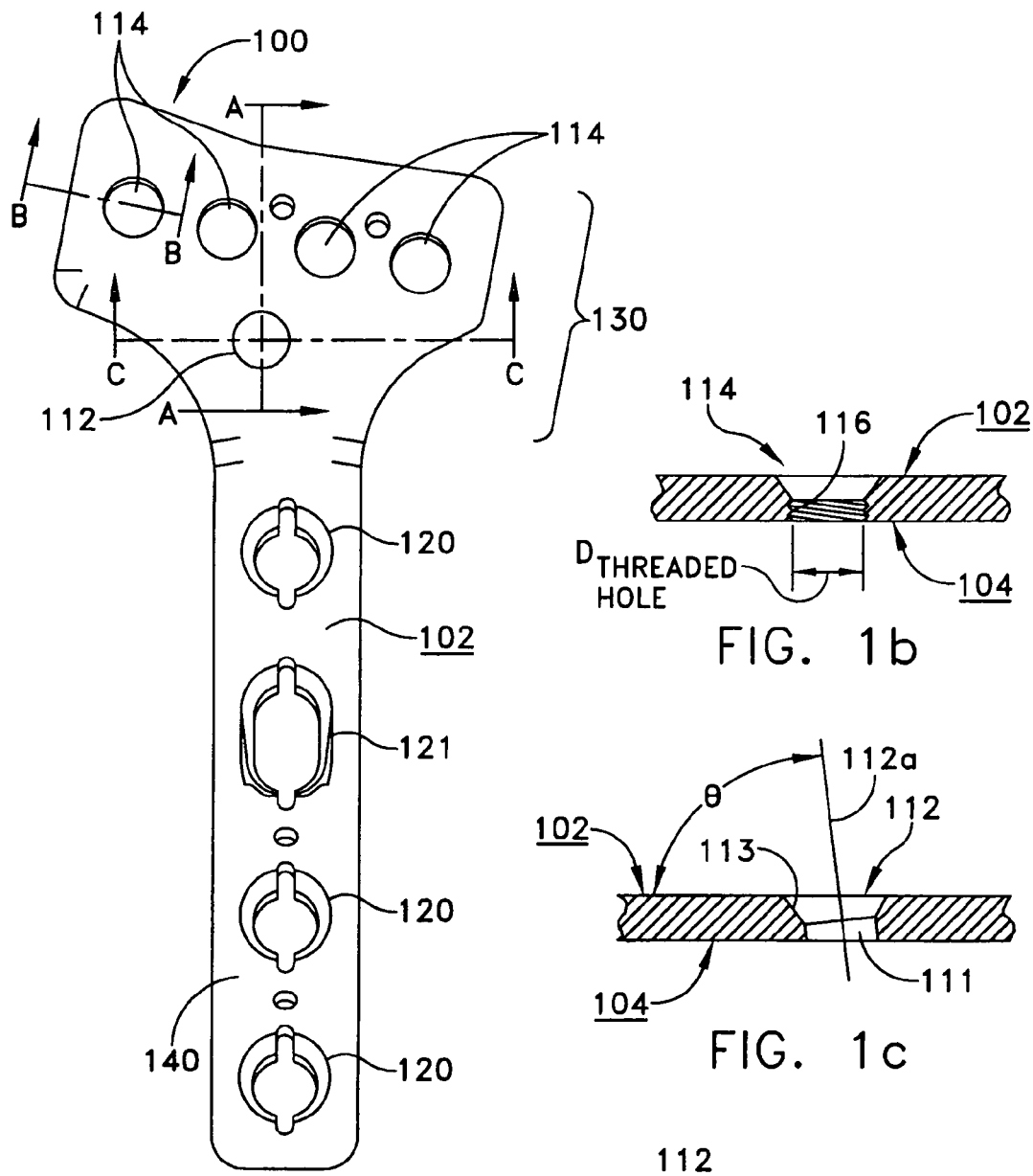

The features shown in the above referenced drawings are not intended to be drawn to scale nor are they intended to be shown in precise positional relationship.

DETAILED DESCRIPTION OF THE INVENTION

Bone plating system formed in accordance with one embodiment of the invention includes a bone plate, locking bone screws, and non-locking bone screws. FIGS. 1a through 4 show an exemplary bone plate 100 according to an aspect of the present invention designed for use in the distal radius volar region. Bone plate 100 has an upper surface 102, a lower surface 104, which is generally the bone-contacting surface, a head portion 130, and a shaft portion 140.

Bone plate 100 has a plurality of plate holes for receiving bone screws in both head portion 130 and shaft portion 140. The plate holes in head portion 130 comprise threaded plate holes 114 for receiving locking bone screws 10. As shown in FIG. 1b, each of threaded plate holes 114 has a diameter $D_{threaded-hole}$, a thread 116 on the sidewall of bone plate 100 that defines threaded plate holes 114 for mating with a locking bone screw 10 (shown in FIG. 5). At least one of the plate holes in head portion 130, however, is a non-threaded plate hole 112 specifically configured and dimensioned for receiving a non-locking cancellous bone screw 20 (shown in FIG. 6). Shaft portion 140 of bone plate 100 is provided with a plurality of shaft plate holes 120, 121. Shaft plate holes 120, 121 also are not threaded, but unlike non-threaded plate holes 112, shaft plate holes 120, 121 are configured and dimensioned to receive standard cortical bone screws 30 (shown in FIG. 7) and generally have a larger diameter than non-threaded plate holes 112. Shaft plate hole 121 may have an elongate shape to accommodate variable positioning of a standard cortical bone screw 30.

Shown in FIGS. 1c and 1d are cross-sectional views of non-threaded plate hole 112 of FIG. 1a through lines A—A and B—B, respectively. Non-threaded plate hole 112 has a diameter $D_{no-thread}$, a sidewall 111, and a countersink 113. Non-threaded plate hole 112 is defined through bone plate 100 at an angle θ with respect to the bone plate so that when non-locking cancellous bone screw 20 is inserted into plate hole 112, it is generally angled distally, i.e. away from the distal end of the radius bone. In an exemplary embodiment comprising a distal radius volar plate 100, angle θ is about 18 degrees from the longitudinal axis 112a of non-threaded plate hole 112 (FIG. 1c). Threaded holes 114 in head portion 130 are often also angled toward the proximal by between 5 degrees and 20 degrees, with about 11 degrees being preferred in many applications.

Figure 1E:
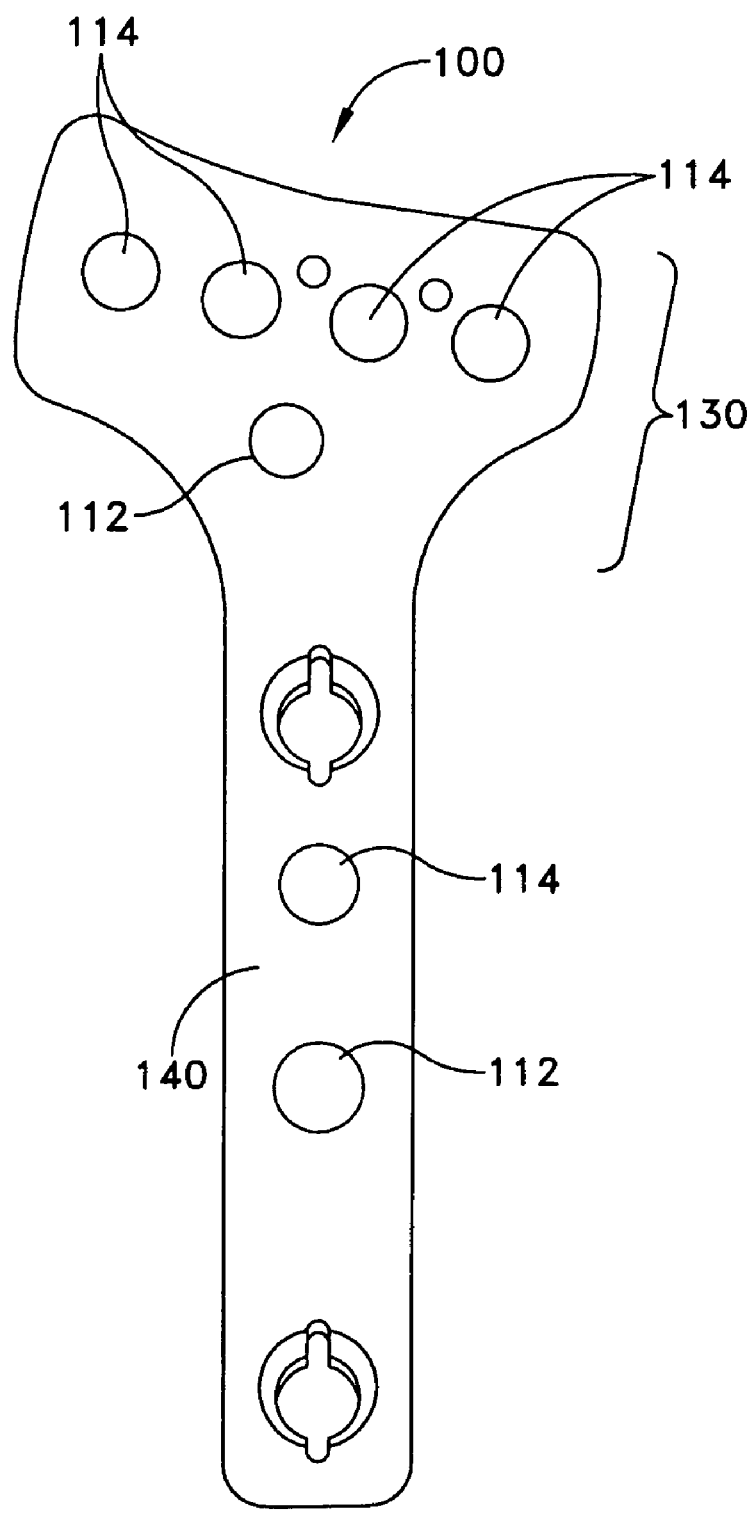
Figure 2:
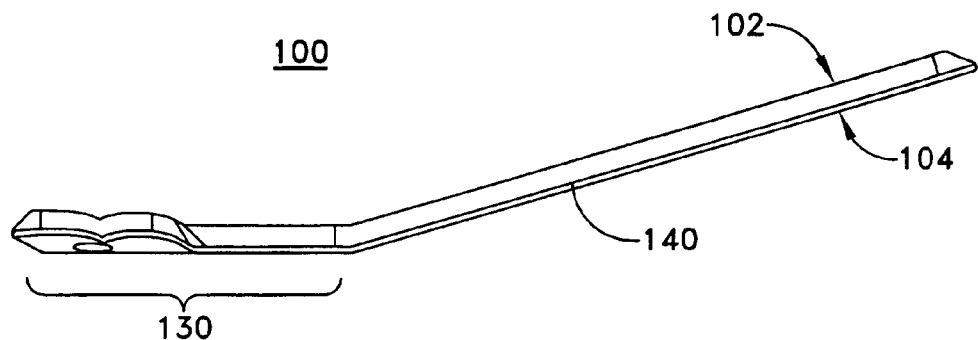
Figure 3:
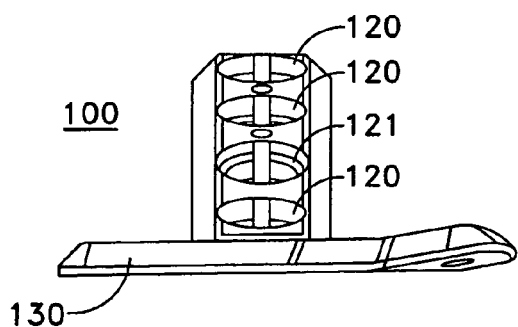
Figure 4:
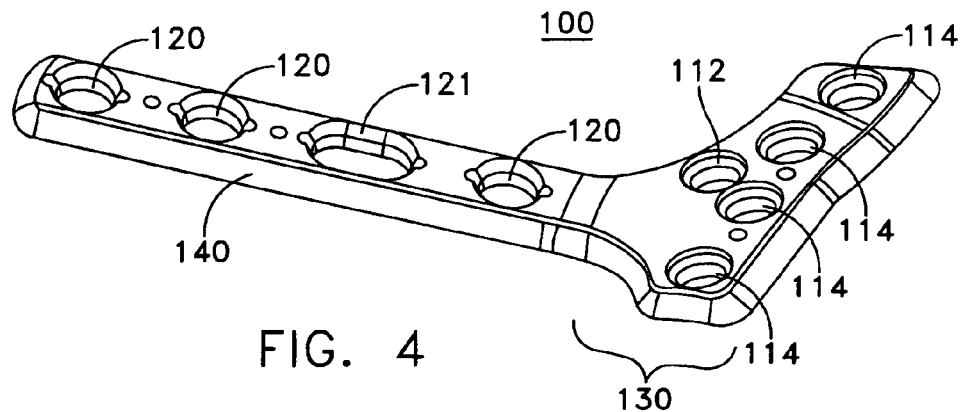

As shown in FIG. 1e, shaft portion 140 of bone plate 100 may have both threaded plate holes 114 and non-threaded shaft plate holes 120, 121 so that both locking and non-locking screws can be used in shaft portion 140. The ability to use locking bone screws in shaft portion 140 is particularly useful when the far cortex of part of the diaphysis is missing or severely damaged. This is helpful since fixation with non-locking screws can be problematic depending upon the condition of the opposing cortex. In such situations, providing one or more non-threaded plate holes 112 in shaft portion 140 can further enhance fixation. Non-locking cancellous bone screws 20 can be used in conjunction with one or more non-threaded plate holes 112 to thread into the cancellous bone in the diaphysis of the bone.

Figure 5:
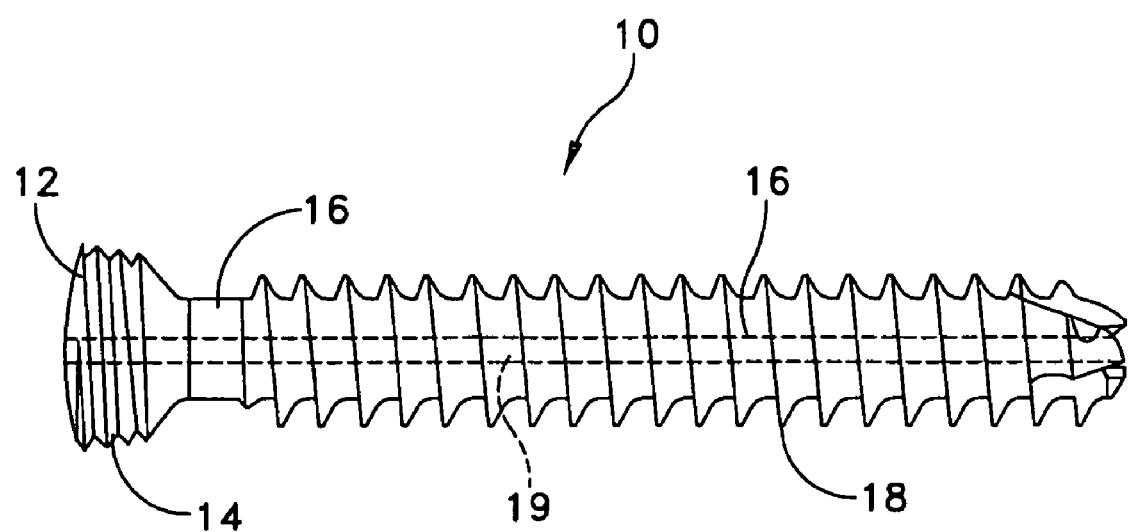
FIG. 5 is a side view of one embodiment of a locking bone screw according to the present invention.

FIG. 5 shows an example of a locking bone screw 10 that may be used with the present invention. It is a surgical bone screw that has a head 12 with threads 14. Head 12 and threads 14 are of an appropriate size and geometry for locking engagement with threaded plate holes 114 of bone plate 100. Threads 14 mate with threads 116 of threaded plate holes 114. Locking screw 10 has a shaft 16 that is at least partially threaded with threads 18 for engaging bone. As is well known in the art, threads 18 and the tip of screw 10 may be self-tapping and/or self-drilling type to facilitate implantation. Shaft 16 may be cannulated with a channel 19 for receiving a guide wire. Thread 14 on head 12 of locking bone screw 10 and thread 116 on threaded plate hole 114 of bone plate 100 lock by interference fit, i.e., a frictional engagement between the threads that acts to store energy in each.

Figure 6:
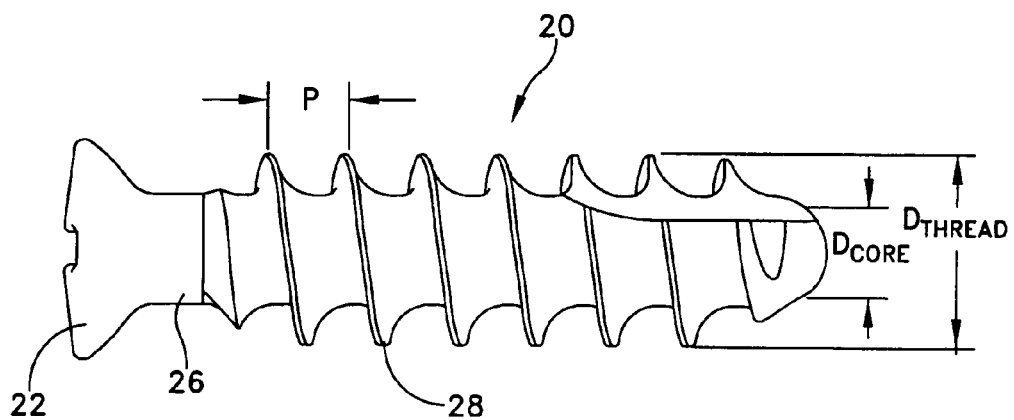
FIG. 6 is a side view of one embodiment of a non-locking bone screw according to the present invention.

Referring to FIG. 6, a non-locking cancellous bone screw 20 is used in conjunction with the specifically configured non-threaded plate hole(s) 112 of bone plate 100. Non-locking cancellous bone screw 20 has a shaft 26 that is at least partially threaded with cancellous threads 28 for engaging the cancellous tissue of the metaphysis region of a bone and a head 22. Non-locking cancellous bone screw 20 has a core diameter, $D_{core}$, a thread diameter, $D_{thread}$, and a thread pitch, P. As is well known in the art, cancellous threads 28 and the tip of cancellous bone screw 20 may be self-tapping and/or self-drilling type to facilitate insertion. Shaft 26 may also be cannulated with a channel for receiving a guide wire to aid in proper screw placement. The use of non-locking cancellous bone screws 20 in non-threaded plate hole(s) 112 in head portion 130 of bone plate 100 promotes better compression between the bone and the bone plate in the metaphysis region of the bone.

Figure 8:
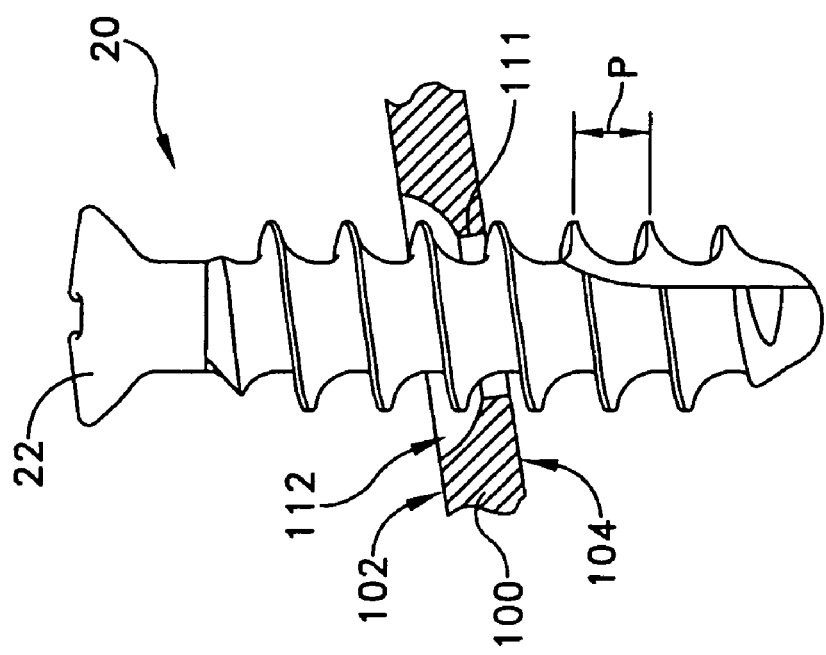

According to a preferred embodiment of the invention, non-locking cancellous bone screw 20 and non-threaded plate hole 112 are configured and dimensioned to have a particular dimensional relationship. Non-locking cancellous bone screw 20 is characterized by a core diameter $D_{core}$, a thread diameter $D_{thread}$, and a thread pitch P. The diameter $D_{no-thread}$ of non-threaded plate hole 112 is dimensioned to be larger than the core diameter $D_{core}$ but smaller than the thread diameter $D_{thread}$ of the non-locking cancellous bone screw 20. Also, the thread diameter $D_{thread}$ is larger than the diameter $D_{no-thread}$ of non-threaded plate hole 112. Although the thread diameter $D_{thread}$ is larger than the diameter of non-threaded plate hole 112, the pitch P of non-locking bone screw's cancellous thread 28 is sufficiently larger than the thickness of sidewalls 111 of bone plate 100 that define non-threaded plate holes, that cancellous thread 28 can thread through non-threaded plate hole 112. Furthermore, the thread pitch P and the thickness of sidewalls 111 are such that non-locking bone screw 20 can be threaded through non-threaded plate hole 112 at a varying angle of about five degrees to about twenty-five degrees from the longitudinal axis 112a (shown in FIG. 1c) of non-threaded plate hole 112, with angles in the range of between fourteen degrees and sixteen degrees being preferred for many applications. This aids in the positioning and fixation of the fragments located in this area of the fracture. The foregoing angular relationships also are preferred due to the location of the hole in the plate which allows for clearance of anatomical structures, such as articular surfaces or opposing cortices. An example of the angular relationship between non-locking bone screw 20 and non-threaded plate hole 112 is illustrated in the cross-sectional drawing of FIG. 8. Because non-locking cancellous bone screw 20 can be threaded into non-threaded plate hole 112 at a varying angle, e.g., between fourteen and sixteen degrees, a surgeon may select an insertion angle for non-locking cancellous bone screw 20 that is optimal for the particular fracture in order to compress the metaphysis region of the bone to the head portion of bone plate 100. Also, the core diameter $D_{core}$ of the non-locking cancellous bone screw 20 is larger than the diameter $D_{threaded-hole}$ of threaded plate hole 114 thus preventing non-locking bone screw 20 from being threaded into threaded plate holes 114.

Figure 7:
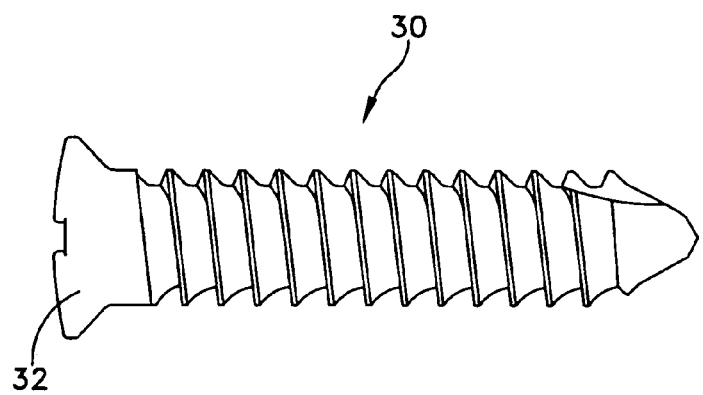
Figure 9:
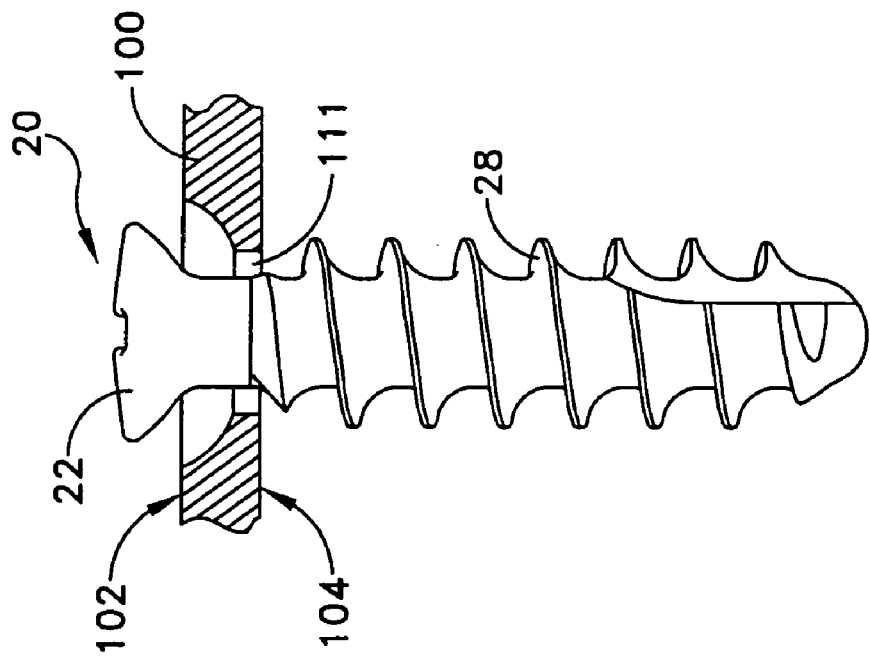
FIG. 9 is a cross-sectional illustration of the non-locking bone screw of FIG. 6 threaded into the non-threaded plate hole of the bone plate of FIG. 1b.

FIG. 7 shows an example of a standard cortical screw 30 that may be used in conjunction with shaft plate holes 120, 121 of bone plate 100. Cortical screws 30 may comprise any conventional cortical bone screw that has a non-threaded head 32 of an appropriate size and geometry for engagement with the portion of bone plate 100 that defines shaft plate holes 120, 121.

Figure 10:
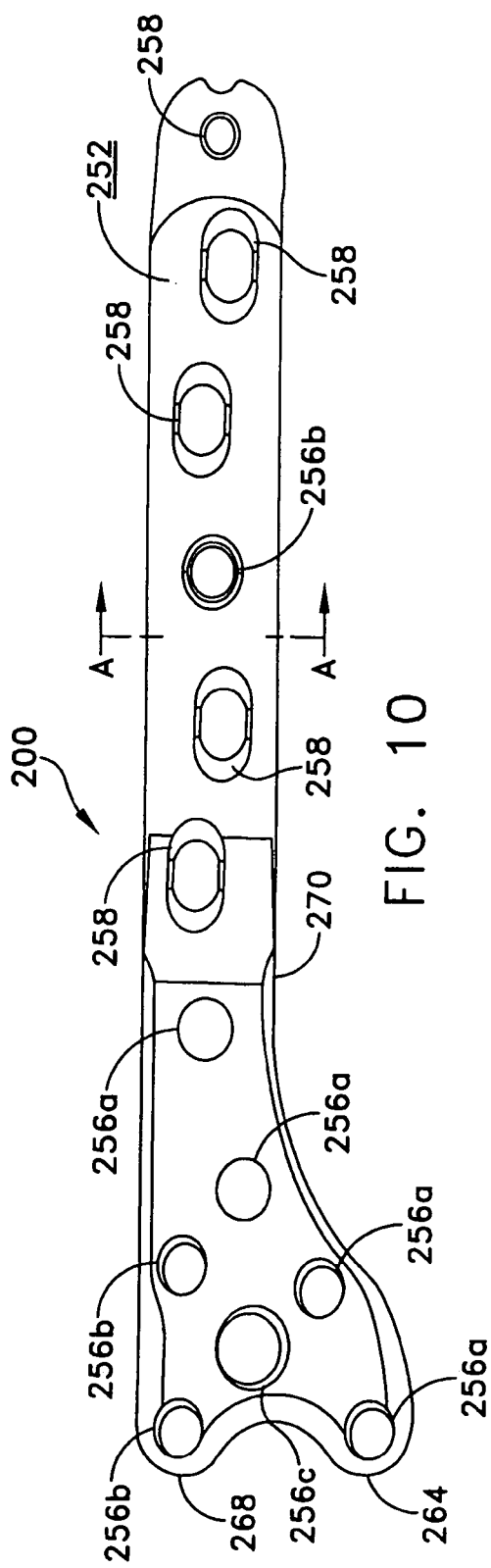
FIG. 10 is a top plan view illustration of another bone plate according to another aspect of the present invention.
Figure 11:
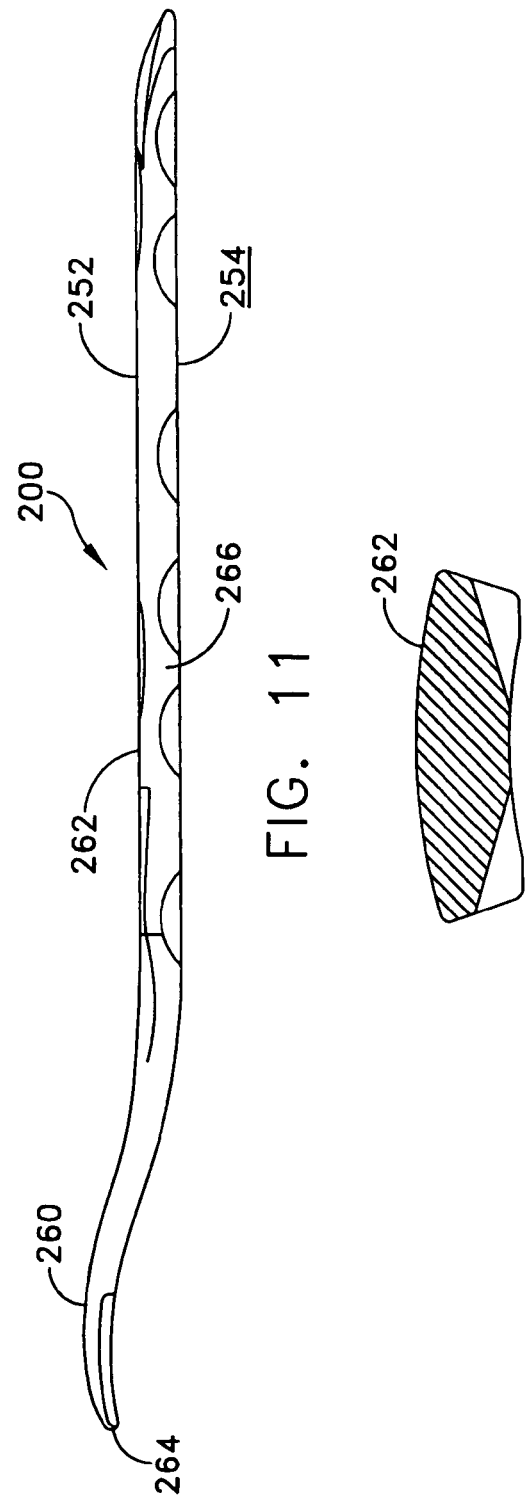
FIG. 11 is a side view of the bone plate of FIG. 10.
Figure 12:
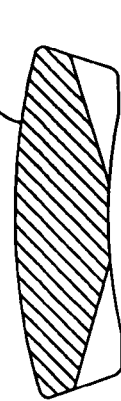
FIG. 12 is a cross-sectional view of the bone plate of FIG. 10 through line A—A.

According to the present invention, the bone plate utilized in the bone plating system is not limited to, e.g., a distal radius volar bone plate 100. The bone plate may be made in different shapes and sizes for use in a wide variety of clinical applications. For example, FIGS. 10–12 show a bone plate 200 according to another aspect of the bone plating system of the present invention specifically designed for use in the distal femur. Bone plate 200 would be used primarily for, but not limited to, severely comminuted fractures including Hoffa type fractures.

Bone plate 200 has an upper surface 252 and a bone-contacting lower surface 254. The bone plate 200 has a plurality of threaded plate holes 256b, 256c (collectively referred to as threaded plate holes 256) for receiving locking bone screws 10. Bone plate 200 also includes a plurality of non-threaded shaft plate holes 258 for receiving standard non-locking bone screws 30. Each of threaded plate holes 256 and non-threaded shaft plate holes 258 pass through upper 252 and bone-contacting surfaces 254. The thread on the portion of bone plate 100 that defines threaded plate holes 256 mates with threaded head 12 of locking bone screw 10 to secure locking screw 10 to bone plate 200 at a temporally fixed angular orientation. Insertion of non-locking screws 30 in non-threaded plate holes 258 draws the bone toward bone-contacting surface 254 so as to compress the bone.

Bone plate 200 also includes one or more non-threaded plate holes 256a for receiving non-locking cancellous bone screws 20. In exemplary bone plate 200, non-threaded plate holes 256a are provided in head portion 260. This allows the fixation of the fracture in the metaphysis region of the distal femur by allowing non-locking cancellous bone screws 20 to provide compression of the bone to the bone plate 200 in that region of the bone. This structure is advantageous since locking bone screws 10 are not very effective in compressing the bone.

Head portion 260 of bone plate 200 is configured and dimensioned to conform to the metaphysis of the distal femur and a shaft portion 262 configured and dimensioned to conform to a diaphysis of a bone. As best seen in FIG. 11, bone contacting surface 254 of head portion 260 is a curved surface so as to fit the contours of the distal femur. Head portion 260 includes an anterior fork 268 substantially parallel to an anterior side 266 of shaft portion 262 and a posterior fork 264 extending laterally out from a posterior side 270 of shaft portion 262. Shaft portion 262 may have both threaded plate holes 256b and non-threaded plate holes 258 so that both locking and non-locking screws can be used in shaft portion 262. The ability to use locking bone screws in shaft portion 262 is particularly useful when the far cortex of part of the diaphysis is missing or severely damaged. Here again the surgeon gains an advantage with the present invention since fixation with non-locking screws under these circumstances is problematic. In such situation, providing one or more of non-threaded plate holes 256a in shaft portion 262 can further enhance fixation. Non-locking cancellous bone screws 20 can be used in conjunction with one or more non-threaded plate holes 256a to thread into the cancellous bone of the diaphysis of the bone. As best seen in FIG. 12, the regions between threaded plate hole 256b and non-threaded shaft plate holes 258 may have a trapezoidal cross section that limits contact between bone-contacting surface 254 of shaft portion 262 and the femur.

Threaded plate holes 256b, 256c in head portion 260 may have different diameters. Plate hole 256c is often surrounded by threaded plate holes 256b, and has a larger diameter to accommodate a locking screw with a larger diameter. Threaded plate holes 256b, 256c preferably are bored in bone plate 200 so that the inserted locking bone screws converge towards one another. It should be noted that, if a surgeon elects, non-locking bone screws may be used in any of threaded plate holes 256.

The bone plating system of the present invention incorporating a long bone plate, such as a distal radius volar plate 100 and distal femur plate 200, is used in the following manner. First the fracture is reduced near the metaphysis of the bone to bring bone fragments in close apposition. Then either bone plate 100 or 200 is positioned and temporarily secured to the bone using K-wires. Next, at least one locking bone screw 10 is inserted into one of threaded plate holes 114, 256b, 256c and screwed into one of the bone fragments in the metaphysis region of the bone. Locking bone screw 10 is then locked at a fixed angular relationship to bone plate 100, 200 fixating the fractured bone in the metaphysis region. One or more of standard cortical screws 30 are then inserted into shaft plate holes 120, 121, 258, and screwed into the diaphysis of the bone thereby compressing the diaphysis of the bone against shaft portion 140, 262 of bone plate 100, 200. Next, one or more non-locking cancellous bone screws 20 are threaded through at least one non-threaded plate hole 112, 256a and into the metaphysis region of the bone. Because locking screws 10 are not very effective at compressing the bone to bone plate 100, 200, the introduction of non-locking cancellous bone screws 20 will achieve the desired compression of the bone to the bone plate at head portion 130, 260 of bone plate 100, 200.

Alternatively, after at least one locking bone screws 10 is inserted into one of threaded plate holes 114, 256b, 256c, and screwed into one of the bone fragments in the metaphysis region of the bone, and locked at a fixed angular relationship to the bone plate 100, 200, one or more non-locking cancellous bone screws 20 may be threaded through at least one non-threaded plate hole 112, 256a and into the metaphysis region of the bone next. Then, one or more of standard cortical screws 30 may be inserted into shaft plate holes 120, 121, 258 and screwed into the diaphysis of the bone compressing the diaphysis of the bone against shaft portion 140, 262 of bone plate 100, 200.

After the bone plating system of the present invention is implanted in a patient, the locking and non-locking bone screws remain seated in their respective plate holes for substantially as long as the bone plate is implanted in order to maximize the benefits of combining non-locking bone screws with locking bone screws.

It is to be understood that the present invention is by no means limited only to the particular constructions herein disclosed and shown in the drawings, but also comprises any modifications or equivalents within the scope of the claims.

What is claimed is:

1. A bone plating system for fixation of bone comprising:
   a bone plate having:
   an upper surface;
   a lower surface;
   at least one non-threaded plate hole having a sidewall;
   at least one threaded plate hole;
   at least one locking bone screw having a shaft with a first thread for engaging bone and a head with a second thread configured and dimensioned to mate with the thread of the threaded plate hole; and
   at least one non-locking cancellous bone screw having a shaft with a cancellous thread for engaging the cancellous tissue of the bone and a head whose diameter is larger than the non-threaded plate hole diameter, wherein the locking and non-locking bone screws remain seated in their respective plate holes for substantially as long as the bone plate is implanted,
   wherein the at least one non-locking cancellous bone screw has a core diameter smaller than the non-threaded plate hole diameter, and the cancellous thread has a diameter larger than the non-threaded plate hole diameter, and a thread pitch that is sufficiently large to clear the sidewall of the non-threaded plate hole.

2. The bone plating system of claim 1 wherein the non-locking bone screw's core diameter is larger than the threaded plate hole diameter, thus preventing the non-locking bone screw from being threaded into the threaded plate holes.

3. The bone plating system of claim 1 wherein the locking bone screw is a self-tapping screw.

4. The bone plating system of claim 1 wherein the locking bone screw is a self-drilling screw.

5. The bone plating system of claim 1 wherein the locking bone screw is cannulated with a channel for insertion of a guide wire to guide screw placement.

6. The bone plating system of claim 1 wherein the non-locking bone screw is at least one of a self-tapping screw and a self-drilling screw.

7. The bone plating system of claim 1 wherein the head portion of the bone plate flares outward from the shaft.

8. The bone plating system of claim 1 wherein the head portion of the bone plate has a curved surface and includes an anterior fork, with a posterior fork extending out from a posterior side of the shaft portion.

9. The bone plating system of claim 1 wherein the shaft portion of the bone plate has a trapezoidal shaped cross-section in regions between the threaded and non-threaded plate holes.

10. A bone plating system for fixation of bone comprising:
    a bone plate having:
    an upper surface;
    a lower surface;
    a head portion;
    a shaft portion;
    at least one non-threaded plate hole having a sidewall and at least one threaded plate hole in the head portion;
    at least one locking bone screw having a shaft with a first thread for engaging bone and a head with a second thread configured and dimensioned to mate with the thread of the threaded plate hole; and
    at least one non-locking cancellous bone screw having a shaft with a cancellous thread for engaging the cancellous tissue of the bone and a head whose diameter is larger than the non-threaded plate hole diameter, wherein the locking and non-locking bone screws remain seated in their respective plate holes for substantially as long as the bone plate is implanted,
    wherein the at least one non-locking cancellous bone screw has a core diameter smaller than the non-threaded plate hole diameter, and the cancellous thread has a diameter larger than the non-threaded plate hole diameter, and a thread pitch that is sufficiently large to clear the sidewall thickness of the non-threaded plate hole.

11. The bone plating system of claim 10 wherein the non-locking bone screw's core diameter is larger than the threaded plate hole diameter, thus preventing the non-locking bone screw from being threaded into the threaded plate holes.

12. The bone plating system of claim 10 further comprising at least one non-threaded plate hole and at least one threaded plate hole in the shaft portion of the bone plate.

13. The bone plating system of claim 10 wherein the locking bone screw is at least one of a self-tapping screw and a self-drilling screw.

14. The bone plating system of claim 10 wherein the locking bone screw is cannulated with a channel for inserting a guide wire to guide screw placement.

15. The bone plating system of claim 10, wherein the non-locking bone screw is a self-tapping screw.

16. The bone plating system of claim 10 wherein the non-locking bone screw is a self-drilling screw.

17. The bone plating system of claim 10 wherein the head portion of the bone plate flares outward from the shaft.

18. The bone plating system of claim 10 wherein the head portion of the bone plate has a curved surface and includes an anterior fork, with a posterior fork extending out from a posterior side of the shaft portion.

19. The bone plating system of claim 10 wherein the shaft portion of the bone plate has a trapezoidal shaped cross-section in regions between the threaded and non-threaded plate holes.

20. The bone plating system of claim 10 further comprising:
- at least one non-threaded plate hole and at least one threaded plate hole provided in the shaft portion of the bone plate;
- at least one additional locking bone screw for mating with the thread of the at least one threaded plate hole provided in the shaft portion of the bone plate; and
- at least one additional non-locking cancellous bone screw for threading through the non-threaded plate hole provided in the shaft portion of the bone plate and engaging the cancellous tissue of the bone.

* * * * *